United States Patent
Fares et al.

(10) Patent No.: US 10,226,415 B2
(45) Date of Patent: Mar. 12, 2019

(54) ANTIPERSPIRANT/DEODORANT COMPOSITIONS

(75) Inventors: Hani M. Fares, Somerset, NJ (US); Donald I. Prettypaul, Englewood, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 126 days.

(21) Appl. No.: 14/001,901

(22) PCT Filed: Mar. 2, 2012

(86) PCT No.: PCT/US2012/027491
§ 371 (c)(1),
(2), (4) Date: Aug. 28, 2013

(87) PCT Pub. No.: WO2012/122021
PCT Pub. Date: Sep. 13, 2012

(65) Prior Publication Data
US 2013/0336912 A1    Dec. 19, 2013

Related U.S. Application Data

(60) Provisional application No. 61/450,303, filed on Mar. 8, 2011.

(51) Int. Cl.
*A61K 8/81* (2006.01)
*A61Q 15/00* (2006.01)

(52) U.S. Cl.
CPC .......... *A61K 8/8164* (2013.01); *A61K 8/8194* (2013.01); *A61Q 15/00* (2013.01)

(58) Field of Classification Search
None
See application file for complete search history.

(56) References Cited

U.S. PATENT DOCUMENTS

| | | | | |
|---|---|---|---|---|
| 5,292,530 A | * | 3/1994 | McCrea | A61K 8/25 252/363.5 |
| 5,370,874 A | * | 12/1994 | Conway | A61K 8/11 424/401 |
| 6,616,921 B2 | * | 9/2003 | Rieley | A61K 8/042 424/400 |
| 2007/0292375 A1 | * | 12/2007 | Woehrmann | A61K 8/4926 424/68 |
| 2009/0016978 A1 | * | 1/2009 | Courtois | A61K 8/8152 424/65 |

OTHER PUBLICATIONS

International Search Report, PCT/US2012/027491, published on Sep. 13, 2012.

* cited by examiner

*Primary Examiner* — Bethany P Barham
*Assistant Examiner* — Dominic Lazaro
(74) *Attorney, Agent, or Firm* — William J. Davis; Nathalie Tietcheu

(57) ABSTRACT

Disclosed are new and improved antiperspirant/deodorant compositions and methods of reducing perspiration, where the new and improved antiperspirant/deodorant compositions contain a water dispersible organic polymer and can reduce the concentration of active antiperspirant ingredients while maintaining antiperspirant efficacy.

8 Claims, No Drawings

ANTIPERSPIRANT/DEODORANT COMPOSITIONS

CROSS REFERENCE TO RELATED APPLICATIONS

This application is the national stage of PCT Application No. PCT/US2012/027491 filed Mar. 2, 2012, which claims priority from Provisional Patent Application No. 61/450,303, filed Mar. 8, 2011, the entire disclosures of which are hereby incorporated in their entirety.

FIELD

The present teachings relate to antiperspirant/deodorant compositions and methods of reducing perspiration. More particularly, the present teachings relate to new and improved antiperspirant/deodorant compositions containing a water dispersible organic polymer.

BACKGROUND

Antiperspirant products typically use aluminum and zirconium-based salts as the active antiperspirant ingredient to control perspiration and malodor. However, such active antiperspirant ingredients can be perceived negatively by consumers due to health and environmental concerns. Moreover, the use of high concentrations of such active antiperspirant ingredients can cause irreversible staining of clothing.

The above issues have been addressed in a number of ways including the addition to an antiperspirant composition of a water soluble polymer comprising Brønsted acid groups. See, e.g., U.S. Pat. No. 6,616,921; U.S. Patent Application Publication No. 2005/0100521 A1; and International Publication No. WO 02/49590 A2. However, in the only issued patent, it is required that the water soluble polymers form true solutions in water, where a true solution typically has an absorbance of less than 0.2, preferably less than 0.1 (for a 1 cm path length at 600 nm).

Accordingly, there is a need for new antiperspirant/deodorant compositions that can reduce the high concentrations of conventional antiperspirant and deodorant ingredients while maintaining antiperspirant efficacy. In addition, there is a need for a new class of polymers that can be used in conjunction with lower concentrations of active antiperspirant ingredients in antiperspirant/deodorant compositions.

SUMMARY

In light of the foregoing, the present teachings provide new and improved antiperspirant/deodorant compositions that can address the various deficiencies and shortcomings of the prior art, including those outlined above. More specifically, the antiperspirant/deodorant compositions and methods of the present teachings, which control perspiration and malodor of a human, use a water dispersible organic polymer as described herein. In particular, inclusion of a water dispersible organic polymer in an antiperspirant/deodorant composition can permit use of a lower concentration of an active antiperspirant ingredient while maintaining antiperspirant efficacy or being extra effective. Moreover, use of lower amounts of active antiperspirant ingredients can result in a cost savings in connection with the manufacture of the product.

The antiperspirant/deodorant compositions of the present teachings can take the form of sticks, fluids, gels, lotions, creams, roll-ons, aerosols, and powders.

Suitable active antiperspirant ingredients include organic compounds or inorganic salts, including aluminum, zirconium or zinc salts, and mixtures thereof. The active antiperspirant ingredient preferably is a coordination complex of aluminum zirconium tetrachlorohydrate and glycine.

Water dispersible organic polymers of the present teachings are organic polymers which do not form true solutions with water and can have an acid value greater than zero. Water dispersible organic polymers include homopolymers, copolymers and higher order polymers as well as their crosslinked counterparts. Water dispersible organic polymers often contain carboxylic acid groups, and at times, can contain latent acid groups which can be hydrolyzed after polymerization or during use of the antiperspirant/deodorant composition.

The foregoing as well as other features and advantages of the present teachings will be more fully understood from the following figures, description, examples, and claims.

DETAILED DESCRIPTION

It now has been discovered that antiperspirant/deodorant compositions which contain a water dispersible organic polymer can maintain antiperspirant efficacy or be extra effective with reduced concentrations of an active antiperspirant ingredient. Consequently, the environmental exposure to high concentrations of aluminum- and zirconium-based compounds as well as the cost of manufacture can be reduced.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," "having," "contain," "contains," or "containing" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

It should be understood that the order of steps or order for performing certain actions is immaterial so long as the present teachings remain operable. Moreover, two or more steps or actions may be conducted simultaneously.

As used herein, "antiperspirant efficacy" refers to at least a 20% reduction in sweat production in about 50% of a given population (as similarly defined by the Food and Drug Administration ("FDA")). To claim commercially antiperspirant activity in the United States, the concentration of active antiperspirant ingredient must achieve at least a 20% reduction in sweat production of at least 50% of the population with a Wilcoxon signed-rank test at a significance level of 0.05. For antiperspirant compositions that demonstrate at least a 30% percent reduction in sweat production, the FDA permits labeling that states, "extra effective."

As used herein, a "polymer" refers to a molecule including a plurality of one or more repeat units or monomers connected by covalent chemical bonds. A polymer can be represented by the general formula:

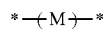

wherein M is the repeat unit or monomer. The degree of polymerization can range from 2 to greater than 10,000. The polymer can have only one type of repeat unit as well as two or more types of different repeat units. When a polymer has only one type of repeat unit, it can be referred to as a homopolymer. When a polymer has two or more types of different repeat units, the term "copolymer" or "copolymeric compound" can be used instead. The polymer can be linear or branched. Branched polymers can include dendritic polymers, such as dendronized polymers, hyperbranched polymers, brush polymers (also called bottle-brushes), and the like. Unless specified otherwise, the assembly of the repeat units in the copolymer can be head-to-tail, head-to-head, or tail-to-tail. In addition, unless specified otherwise, the copolymer can be a random copolymer, an alternating copolymer, or a block copolymer.

A polymer has a "backbone" or a "backbone chain," which is a series of covalently bonded atoms that together form a nearly continuous chain of atoms connecting the repeating units or monomers used to form the polymer. A "pendant group" or a "side chain" of a polymer is a group not part of or apart from the backbone chain of the polymer. Pendant groups typically contain functionality that can facilitate the polymerization reaction, for example, formation of the polymer backbone. Pendant groups also can be selected to be beneficial after polymerization, for example, influencing the properties and characteristics of the resulting polymer.

As used herein, an "organic polymer" refers to a polymer that includes carbon, for example, having a carbon backbone such as from polymerization of ethylene groups of the monomers. The carbon backbone optionally can have heteroatoms and chemical functionality optionally present and interdispersed along the backbone. Such heteroatoms and chemical functionality can include nitrogen, oxygen, silicon, sulfur, phosphorus and selenium; and amide, amino, ether and ester groups, respectively.

As used herein, a "water dispersible polymer" refers to a polymer that is water soluble but does not form a true solution with water, where a true solution is defined as a one percent solution of the polymer in water having an absorbance less than 0.2 at 600 nm when measured along a one centimeter path length at 37° C. using a suitable spectrophotometer. To be clear, although a water dispersible polymer may be soluble in water, even to a high degree, the water dispersible polymer does not form a true solution in water. Defined quantitatively, a one percent aqueous solution of a water dispersible polymer will have an absorbance greater than 0.2 at 600 nm when measured along a one centimeter path length at 37° C. using a suitable spectrophotometer. In certain embodiments, the water dispersible polymer will have an absorbance greater than or equal to about 0.3, greater than or equal to about 0.4, greater than or equal to about 0.5, greater than or equal to 1, greater than or equal to 1.5, or greater than or equal to 2.

In certain embodiments, the water dispersible polymer can have an acid value greater than zero, usually due to the presence of free acid groups, for example, carboxylic acid groups. In some embodiments, the water dispersible polymer can have an acid value greater than about 150, greater than about 200, greater than about 250, greater than about 300, greater than about 350, greater than about 500, greater than about 600, or greater than about 650. In various embodiments, the water dispersible polymer can have an acid value greater than about 700, or greater than about 800.

Accordingly, a water dispersible organic polymer of the present teachings can possess characteristics that typically are identified with water soluble compounds but also can possess characteristics that usually are found in compounds that form dispersions in water or that are partially water soluble. For example, in various embodiments, in addition to the presence of free acid groups, a water dispersible organic polymer optionally can contain other hydrophilic functionality to provide increased water solubility characteristics. Simultaneously, a water dispersible organic polymer can have functionality that adds hydrophobic characteristics, for example, the inclusion of long chain alkyl groups and/or moieties containing aromatic groups.

In some embodiments, the hydrophilic or hydrophobic properties of a polymer can be influenced by modification of a monomer prior to polymerization. For example, maleic anhydride can be functionalized with soybean oil (maleated soybean oil) or castor oil (castoryl maleate) to increase the hydrophobicity of a polymer including such a repeating unit. Castor oil also can be functionalized with maleic anhydride in different positions and/or on different alkylene chains and/or via a carbon-carbon bond or a carbon-oxygen bond. Consequently, the resulting compound can be a mono- or di-acid. In particular embodiments, the hydrophilic or hydrophobic properties of a polymer can be modified after polymerization as discussed elsewhere herein.

An organic polymer can be synthesized to have a particle size and/or a molecular weight large enough to create a dispersion in water and consequently, an absorbance identified with a water dispersible organic polymer. In various embodiments, the molecular weight of an organic polymer can be increased by crosslinking, whether internally or through the use a separate crosslinking agent or crosslinker. The molecular weight of a water dispersible organic polymer can vary widely but typically is in the range of about 10,000 to about 4,000,000, or about 50,000 to about 3,000,000, or about 100,000 to about 2,000,000.

A water dispersible organic polymer can have pendant groups that include free acid groups, for example, carboxylic acid groups, phosphoric acid groups, and sulfonic acid groups. The acid groups can be introduced into the organic polymer by a variety of monomers which contain a free acid group or a latent acid group. That is, a water dispersible organic polymer can comprise a product of a polymerization reaction of a repeating unit containing a free acid group. For example, incorporation of acrylic acid, methacrylic acid, crontonic acid, citraconic acid, maleic acid, methylenesuccinic acid (itaconic acid), cinnamic acid, allocinnamic acid, and/or oleic acid into an organic polymer can provide the free carboxylic acid groups of a water dispersible organic polymer.

In some embodiments, a water dispersible organic polymer can be synthesized using monomers having latent acid groups, which can be hydrolyzed to create free acid groups. Illustrative examples of such monomers include esters and anhydrides including, but not limited to, alkyl acrylates, alkyl methacrylates, maleic anhydride, and citraconic anhydride.

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), butyl (e.g., n-butyl, iso-butyl, sec-butyl, tert-butyl), pentyl (e.g., n-pentyl, iso-pentyl, neopentyl), and hexyl groups.

In particular embodiments, a water dispersible organic polymer can incorporate repeating units of, or comprise a product of a polymerization reaction of a repeating unit of, various unsaturated compounds including, but not limited to, alkyl vinyl ethers, ethylene, isobutylene, propylene, and vinyl acetates. Polymerization of these monomers often is in the presence of another monomer, for example, a monomer containing a free or latent acid group, which polymerization results in a copolymer. For example, an alkyl vinyl ether, such as methyl vinyl ether, dodecyl vinyl ether or octyl vinyl ether, can be copolymerized with a monomer having latent acid groups, for example, maleic anhydride, to produce a copolymer. In addition, maleic anhydride can be polymerized with an alkylene group such as ethylene, isobutylene or propylene, to create a co-polymer that can be further functionalized to create a water dispersible organic polymer.

In addition to co-polymers containing two general repeating units, a water dispersible organic polymer of the present teachings also includes higher order polymers, which can contain three or more repeating units. In other words, three different monomers, each having at least one unsaturated group, can be reacted to provide a higher order polymer which can be a water dispersible organic polymer. For example, two different alkyl vinyl ethers such as methyl vinyl ether and n-dodecyl vinyl ether can be reacted with maleic anhydride to produce an alkyl vinyl ether (1)/alkyl vinyl ether (2)/maleic anhydride polymer (e.g., methyl vinyl ether/n-dodecyl vinyl ether/maleic anhydride polymer). Of course other alkyl vinyl ethers such as methyl vinyl ether or octyl vinyl ether can be used as well as other anhydrides and unsaturated monomers. When preparing co- or higher order polymers, the mole ratio of the various monomers can be varied to adjust the properties of the resulting polymer.

Such co- and higher order polymers can be further functionalized to produce polymers useful in the present teachings. For example, if latent acid groups are present after polymerization, some or all of the latent acid groups can be hydrolyzed to increase the acid value of the polymer. In addition, a polymer derived from, in part, maleic anhydride, can be reacted with an alkyl amine, for example, butylamine, octylamine or dodecylamine, to produce a succinimide derivative which incorporates the alkyl chain into the polymer thereby increasing its hydrophobicity.

As mentioned above, in particular embodiments, a polymer can be crosslinked with a crosslinking agent or crosslinker to modify suitably the properties of an organic polymer to create a water dispersible organic polymer. For example, an alkyl vinyl ether/maleic anhydride copolymer such as methyl vinyl ether/maleic anhydride co-polymer can be crosslinked with a bis-unsaturated compound such as an alkyl diene, for example, decadiene, or a divinyl compound, for example, N,N'-divinylimidazolidone, to provide a water dispersible organic polymer. A crosslinking agent can be used in any amount that provides a suitable water dispersible organic polymer, for example, from about 0.5% to about 10% or greater. In addition to being incorporated into the backbone of a water dispersible organic polymer, anhydrides can be useful as crosslinking agents to create polymer networks.

The characteristics of a water dispersible organic polymer can be modified for particular applications and/or for compatibility with other components in an antiperspirant/deodorant composition. For example, a water dispersible organic polymer can be functionalized along its backbone or on its pendant groups by the inclusion of appropriate chemical functionality, for example, hydroxyl groups for increased water solubility.

Active antiperspirant ingredients suitable for use in the antiperspirant/deodorant compositions of the present teachings can include any compound, composition or other material having antiperspirant activity. Active antiperspirant ingredients include astringent metallic salts, especially the inorganic salts of aluminum zirconium and zinc, as well as mixtures thereof. Depending on the product form and intended use, preferred active antiperspirant ingredients are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the composition include those that conform to the formula: $Al_2(OH)_aCl_b \cdot xH_2O$ where a is from about 2 to about 5; the sum of a and b is about 6; x is from about 1 to about 6; and where a, b, and x may have non-integer values. Preferred are the aluminum chlorohydroxides referred to as "basic chlorohydroxide," wherein a=5, and "2/3 basic chlorohydroxide," wherein a =4.

Zirconium salts for use in the antiperspirant/deodorant compositions include those that conform to the formula: $ZrO(OH)_{2-a}Cl_a \cdot xH_2O$, where a is from about 1.1 to about 2.0; x is from about 1 to about 8; and wherein a and x may both have non-integer values. Preferred zirconium salts are those complexes that additionally contain aluminum and glycine, commonly know as ZAG complexes. These ZAG complexes contain aluminum chlorohydroxide and zirconyl hydroxy chloride conforming to the above described formulas.

More specifically, active antiperspirant ingredients for use in the antiperspirant/deodorant compositions of the present teachings can include: aluminum chloride up to 15%, calculated on the hexahydrate form, in an aqueous solution nonaerosol dosage form; aluminum chlorohydrate up to 25%; aluminum chlorohydrex polyethylene glycol up to 25%; aluminum chlorohydrex propylene glycol up to 25%; aluminum dichlorohydrate up to 25%; aluminum dichlorohydrex polyethylene glycol up to 25%; aluminum dichlorohydrex propylene glycol up to 25%; aluminum sesquichlorohydrate up to 25%; aluminum sesquichlorohydrex polyethylene glycol up to 25%; aluminum sesquichlorohydrex propylene glycol up to 25%; aluminum zirconium octachlorohydrate up to 20%; aluminum zirconium octachlorohydrex gly up to 20%; aluminum zirconium pentachlorohydrate up to 20%; aluminum zirconium pentachlorohydrex gly up to 20%; aluminum zirconium tetrachlorohydrate up to 20%; aluminum zirconium tetrachlorohydrex gly up to 20%; aluminum zirconium trichlorohydrate up to 20%; and aluminum zirconium trichlorohydrex gly up to 20%.

The concentration of the active antiperspirant ingredients will typically range from at least about 0.1%, from at least about 2%, from at least about 3%, or from at least about 5% to no more than about 25%, and preferably no more than about 20%, by weight of the antiperspirant/deodorant composition.

For example, in some embodiments, the antiperspirant/deodorant compositions can have from about 0.1% to about 20% active antiperspirant ingredient, or from about 1% to about 10% active antiperspirant ingredient, or from about 2% to about 7% active antiperspirant ingredient. Because inclusion of a water dispersible organic polymer can permit reduction in the concentrations of active antiperspirant ingredient, in certain embodiments, the antiperspirant/deodorant composition can include about 5% or less active antiperspirant ingredient, or about 4% or less, or about 3% or less, or about 2% or less, or about 1.5% or less, or about 1% or less active antiperspirant ingredient.

In various embodiments, the antiperspirant/deodorant composition can contain about equal amounts of a water dispersible organic polymer and an active antiperspirant ingredient. That is, in some embodiments, the antiperspirant/deodorant composition can contain from 0.1% to about 20%, from about 1% to about 10%, or from about 2% to about 7% active antiperspirant ingredient, and the antiperspirant/deodorant composition can contain from about 0.1% to about 20%, from about 1% to about 10%, or from about 2% to about 7%, respectively, water dispersible organic polymer. Moreover, where in certain embodiments, the antiperspirant/deodorant compositions include about 5% or less active antiperspirant ingredient, or about 4% or less, or about 3% or less, or about 2% or less, or about 1.5% or less, or about 1% or less active antiperspirant ingredient, the antiperspirant/deodorant composition can include about 5% or less, or about 4% or less, or about 3% or less, or about 2% or less, or about 1.5% or less, or about 1% or less, respectively, water dispersible organic polymer. However, in these latter examples where the concentration of the active antiperspirant active is below about 5%, the amount of a water dispersible organic polymer can remain at a concentration of about 5% or higher.

The antiperspirant/deodorant compositions of the present teachings may further comprise other optional materials known for use in antiperspirant, deodorant or other personal care products, including those materials that are known to be suitable for topical application to skin. Non-limiting examples include dyes or colorants, fragrances, emulsifiers, distributing agents, pharmaceuticals or other topical actives, deodorant agents, antimicrobials, preservatives, surfactants, processing aides such as viscosity modifiers and wash-off aids.

The antiperspirant/deodorant compositions of the present teachings can be formulated as any known or otherwise effective product form for providing topical application of an active antiperspirant ingredient and/or an active deodorant ingredient to the desired area of the skin. Non-limiting examples of such product forms include liquids (e.g., aerosols, pump sprays, roll-ons), solids (e.g., gel solids, invisible solids, wax solid sticks) and semi-solids (e.g., creams, soft solids, lotions).

During preparation of an antiperspirant/deodorant composition and/or in the design of product delivery, a water dispersible organic polymer usually is separated from the active antiperspirant ingredient to prevent mixing and premature degradation of one or both of these components. The separation can be effected by maintaining these components in physically separate locations of a package or application device prior to use, or by separating them chemically. For example, if the antiperspirant/deodorant composition is in the form of an emulsion, the active antiperspirant ingredient and the water dispersible organic polymer can be in different phases of the composition. As another example, the active antiperspirant ingredient and the water dispersible organic polymer can be incorporated into a diluent in which each is insoluble.

In various embodiments, the antiperspirant/deodorant composition can be in an anhydrous form, i.e., the antiperspirant product does not contain more than about 10% water, and more likely less than about 7%, or less than about 5% water, or preferably less than about 3%, or less than about 2% water.

The antiperspirant/deodorant products are generally stored in and dispensed from a suitable package or applicator device as is known and used in the art.

The antiperspirant/deodorant compositions of the present teachings can be prepared by any known or otherwise effective technique, suitable for providing an antiperspirant/deodorant composition of the desired form and having the essential materials described herein. Many such techniques are described in the antiperspirant/deodorant formulation arts for the described product forms.

The following examples are provided to illustrate further and to facilitate the understanding of the present teachings and are not in any way intended to limit the invention.

All percentages, parts and ratios are based upon the total weight of the antiperspirant/deodorant compositions of the present teachings and all measurements made are at 25° C., unless otherwise specified.

The concentration of active antiperspirant ingredient in an antiperspirant/deodorant composition can be calculated based on an anhydrous basis, omitting from the calculation any buffer components and water. However, for the below examples, the weight percentage of active antiperspirant ingredient represents the active antiperspirant ingredient as is, for example, including any water and buffer components.

Example 1

Anhydrous Antiperspirant Stick Compositions

Example 1A

Exemplary Anhydrous Antiperspirant Stick Composition

An embodiment of an anhydrous antiperspirant stick composition according to the present teachings was prepared using conventional, known techniques. The anhydrous antiperspirant stick composition had the following formulation:

| Ingredient | % by wgt |
| --- | --- |
| Cyclomethicone[a] | 61 |
| Stearyl alcohol C-18[b] | 20 |
| Hydrogenated castor oil[c] | 2 |
| PEG-100 Stearate & Glyceryl Stearate[d] | 1 |
| Aluminum zirconium tetrachlorohydrex glycenate[e] | 5 |
| Water dispersible organic polymer[f] | 5 |
| Talc 200[g] | 3 |
| PPG 14 butyl ether[h] | 2 |
| Phenethyl Benzoate[i] | 1 |

[a]The Scent Works
[b]Cognis
[c]Castrowax MP70, Performance Materials
[d]Arlacel 165, UniQema
[e]AZG-370, Summit
[f]2,5-Furandione polymer with 1,9 decadiene and methoxy ether (PVM/MA decadiene crosspolymer; CAS 136392-67-1) International Specialty Products (ISP)
[g]Luzenac
[h]Croda
[i]X-Tend 226, ISP The above exemplary antiperspirant composition in the form of a stick was evaluated for effectiveness as an antiperspirant using a modified FDA protocol. The mean and median reductions in the amount of sweat collected due to treatment with the exemplary antiperspirant composition were about 31%. Consequently, statistical analysis determined that the exemplary antiperspirant composition qualified as an antiperspirant as the stick product demonstrated antiperspirant efficacy.

Example 1B

Comparative Anhydrous Antiperspirant Stick Composition

An illustrative comparative anhydrous antiperspirant stick composition was prepared using conventional, known techniques. The comparative anhydrous antiperspirant stick composition had the following formulation, which lacks a water dispersible organic polymer and has over 3.5 times the concentration of active antiperspirant ingredient:

| Ingredient[1] | % by wgt |
| --- | --- |
| Cyclomethicone[j] | 53 |
| Stearyl alcohol C-18 | 20 |
| Hydrogenated castor oil | 2 |
| PEG-100 Stearate & Glyceryl Stearate | 1 |
| Aluminum zirconium tetrachlorohydrex glycenate | 18 |
| Talc 200 | 3 |
| PPG 14 butyl ether | 2 |
| Phenethyl Benzoate | 1 |

[1]All ingredients sourced the same as in Example 1A unless otherwise noted
[j]Dow The above comparative antiperspirant composition in the form of a stick was evaluated for effectiveness as an antiperspirant using a modified FDA protocol. The mean or median reduction in the amount of sweat collected due to treatment with the comparative antiperspirant composition was about 40%.

In comparison to the antiperspirant composition of Example 1A, which had over 3.5 times less active antiperspirant ingredient but 5% of a water dispersible organic polymer, both antiperspirant compositions demonstrated antiperspirant efficacy. Accordingly, an antiperspirant composition of the present teachings demonstrated comparable antiperspirant efficacy to a composition containing greater than 350% more active antiperspirant ingredient but absent a water dispersible organic polymer.

Example 1C

Control Anhydrous Antiperspirant Stick Composition

An illustrative control anhydrous antiperspirant stick composition was prepared using conventional, known techniques. The control anhydrous antiperspirant stick composition had the following formulation, which lacks a water dispersible organic polymer and an active antiperspirant ingredient:

| Ingredient[2] | % by wgt |
| --- | --- |
| Cyclomethicone[j] | 71 |
| Stearyl alcohol C-18 | 20 |
| Hydrogenated castor oil | 2 |
| PEG-100 Stearate & Glyceryl Stearate | 1 |
| Talc 200 | 3 |
| PPG 14 butyl ether | 2 |
| Phenethyl Benzoate | 1 |

[1] All ingredients sourced the same as in Example 1B

The above control antiperspirant composition in the form of a stick was evaluated for effectiveness as an antiperspirant using a modified FDA protocol. The mean or median reduction in the amount of sweat collected due to treatment with the control antiperspirant composition was about 8%.

Example 2

Antiperspirant Roll-On Composition

An embodiment of an antiperspirant roll-on composition according to the present teachings was prepared using conventional, known techniques. The antiperspirant roll-on composition had the following formulation:

| Ingredient | % by wgt |
| --- | --- |
| Cyclopentasiloxane (NF)[k] | 85 |
| Aluminum zirconium tetrachlorohydrex glycenate[l] | 5 |

-continued

| Ingredient | % by wgt |
|---|---|
| Water dispersible organic polymer[m] | 5 |
| Bentone 38 V[n] | 3 |
| Alcohol (SD 40)[o] | 1 |
| Propylene carbonate-NF[p] | 1 |

[k]The Scent Works
[l]AZG-370, Summit
[m]2,5-Furandione polymer with 1,9 decadiene and methoxy ether (PVM/MA decadiene crosspolymer; CAS 136392-67-1) International Specialty Products (ISP)
[n]Elementis
[o]ISP
[p]Huntsman The above exemplary antiperspirant composition in the form of a roll-on was evaluated for effectiveness as an antiperspirant using a modified FDA protocol. The mean and median reductions in the amount of sweat collected due to treatment with the exemplary antiperspirant composition were about 36% and 37%, respectively. Consequently, statistical analysis determined that the exemplary antiperspirant composition qualified as an antiperspirant as the roll-on product demonstrated antiperspirant efficacy.

Example 3

Antiperspirant Aerosol Composition

An embodiment of an antiperspirant aerosol composition according to the present teachings was prepared using conventional, known techniques. The antiperspirant aerosol composition had the following formulation:

| Ingredient | % by wgt |
|---|---|
| Cyclomethicone[q] | 11 |
| Ceraphyl SLK[r] | 15 |
| Bentone 38 V[s] | 2 |
| Propylene glycol | 2 |
| Aluminum chlorohydrate[u] | 5 |
| Water dispersible organic polymer[v] | 5 |
| Propellant Mix | 60 |

[q]ISP
[r]ISP
[s]Elementis
[u]Reach 103, Summit
[v]2,5-Furandione polymer with 1,9 decadiene and methoxy ether (PVM/MA decadiene crosspolymer; CAS 136392-67-1) International Specialty Products (ISP)

Example 4

Antiperspirant Low-Residue Stick Composition

An embodiment of an antiperspirant low-residue stick composition according to the present teachings was prepared using conventional, known techniques. The antiperspirant low-residue stick composition had the following formulation:

| Ingredient | % by wgt |
|---|---|
| Cyclomethicone[aa] | 53.5 |
| Stearyl alcohol C-18[bb] | 20 |
| Hydrogenated castor oil[cc] | 2 |
| PEG-8 Distearate | 1 |
| PPG 14 Butyl ether[ee] | 2 |
| PEG-100 Stearate & Glyceryl Stearate[ff] | 1 |
| Aluminum zirconium tetrachlorohydrex glycenate[gg] | 5 |

| Ingredient | % by wgt |
|---|---|
| Water dispersible organic polymer[hh] | 5 |
| Fumed silica[ii] | 0.5 |
| Phenethyl benzoate[jj] | 3 |
| Isocetyl Stearate[kk] | 2.5 |
| Diisopropyl adipate[ll] | 2.5 |
| Mineral oil[mm] | 1 |
| Fragrance oil | 1 |

[aa]SF1202, General Electric
[bb]Cognis
[cc]Castowax MP80, Performance Chem
[ee]Degussa
[ff]Arlacel 165, UniQema (Croda)
[gg]AZG-370, Summit
[hh]2,5-Furandione polymer with 1,9 decadiene and methoxy ether (PVM/MA decadiene crosspolymer; CAS 136392-67-1) International Specialty Products (ISP)
[ii]Cabosil M-5, Aerosil 200
[jj]X-Tend 226, ISP
[kk]Ceraphyl 494, ISP
[ll]Ceraphyl 230, ISP
[mm]ISP Example 5

Antiperspirant/Deodorant Powder Composition

An embodiment of an antiperspirant low-residue stick composition according to the present teachings was prepared using conventional, known techniques. The antiperspirant low-residue stick composition had the following formulation:

| Ingredient | % by wgt |
|---|---|
| Talc[oo] | 85.3 |
| Aluminum chlorohydrate[pp] | 5 |
| Water dispersible organic polymer[qq] | 5 |
| Fumed silica[rr] | 0.2 |
| Zea mays starch[ss] | 4 |
| Fragrance[tt] | 0.5 |

[oo]Imperial 200 usp, Luzenac America
[pp]ACH, Summit
[qq]2,5-Furandione polymer with 1,9 decadiene and methoxy ether (PVM/MA decadiene crosspolymer; CAS 136392-67-1) International Specialty Products (ISP)
[rr]Aerosil 200, Degussa
[ss]Corn starch
[tt]Firmenich Example 6

Antiperspirant Low-Residue Soft-Solid Composition

Example 6A

Stearyl Alcohol-Based Antiperspirant Low-Residue Soft-Solid Composition

An embodiment of an antiperspirant low-residue soft-solid composition having a stearyl alcohol base was prepared using conventional, known techniques. The antiperspirant low-residue soft-solid composition had the following formulation:

| Ingredient | % by wgt |
| --- | --- |
| Cyclomethicone[a1] | 51.5 |
| Stearyl alcohol C-18[b1] | 10 |
| Hydrogenated castor oil[c1] | 3 |
| PPG 14 Butyl ether[d1] | 12 |
| Dimethicone[e1] | 4 |
| Aluminum zirconium tetrachlorohydrex glycenate[f1] | 5 |
| Water dispersible organic polymer[g1] | 5 |
| Fumed silica[h1] | 1 |
| C12-C15 alkyl benzoate | 4 |
| Procetyl 14L[j1] | 2 |
| Petrolatum[k1] | 1.5 |
| Fragrance oil | 1 |

[a1]SF1202, General Electric
[b1]Cognis
[c1]Castowax MP80, Performance Chem
[d1]Degussa
[e1]1000, Dow
[f1]AZG-370, Summit
[g1]2,5-Furandione polymer with 1,9 decadiene and methoxy ether (PVM/MA decadiene crosspolymer; CAS 136392-67-1) International Specialty Products (ISP)
[h1]Cabosil M-5, Aerosil 200
[j1]ISP
[k1]ISP

Example 6B

Wax-Based Antiperspirant Low-Residue Soft-Solid Composition

An embodiment of an antiperspirant low-residue soft-solid composition having a wax base was prepared using conventional, known techniques. The antiperspirant low-residue soft-solid composition had the following formulation:

| Ingredient | % by wgt |
| --- | --- |
| Cyclomethicone[m1] | 55 |
| Tribehinin[n1] | 5 |
| PPG 14 Butyl ether[o1] | 8 |
| Aluminum zirconium tetrachlorohydrex glycenate[p1] | 5 |
| Water dispersible organic polymer[q1] | 5 |
| Talc 200[r1] | 3 |
| Fumed silica[s1] | 1 |
| C12-C15 alkyl benzoate[t1] | 5 |
| Procetyl 141[u1] | 2 |
| Ozokorite wax[v1] | 4 |
| Microcrystalline wax[w1] | 5 |
| Petrolatum[x1] | 1 |
| Fragrance oil | 1 |

[m1]SF1202, General Electric
[n1]Syncrowax HRS C, Croda
[o1]Degussa
[p1]AZG-370, Summit
[q1]2,5-Furandione polymer with 1,9 decadiene and methoxy ether (PVM/MA decadiene crosspolymer; CAS 136392-67-1) International Specialty Products (ISP)
[r1]Luzenac
[s1]Cabosil M-5, Aerosil 200
[t1]Finsolv TN
[u1]ISP
[v1]S&P
[w1]S&P
[x1]ISP The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. An antiperspirant/deodorant composition comprising:
   (i) 0.1 wt. % to 20 wt. % of at least one active antiperspirant ingredient; and
   (ii) 7 wt. % to 20 wt. % of a water dispersible organic polymer comprising free carboxylic acid group(s),
   wherein the water dispersible organic polymer
   a) is a 2,5-Furandione polymer with 1,9-decadiene and methoxy ether;
   b) has an acid value greater than 200; and
   c) is separated from the active antiperspirant ingredient.

2. The antiperspirant/deodorant composition of claim 1, wherein said water dispersible organic polymer has an acid value greater than about 350.

3. The antiperspirant/deodorant composition of claim 1, further comprising a second water dispersible organic polymer, wherein said second water dispersible organic polymer comprises a product of a polymerization reaction of acrylic acid, citraconic acid, crotonic acid, maleic acid, methacrylic acid, methylenesuccinic acid, or combinations thereof.

4. The antiperspirant/deodorant composition of claim 1, wherein said second water dispersible organic polymer comprises latent acid groups.

5. The antiperspirant/deodorant composition of claim 1, wherein said second water dispersible organic polymer comprises a product of a polymerization reaction of an alkyl vinyl ether, ethylene, isobutylene, propylene, vinyl acetate, or combinations thereof.

6. The antiperspirant/deodorant composition of claim 5, wherein said alkyl vinyl ether is methyl vinyl ether or ethyl vinyl ether.

7. The antiperspirant/deodorant composition claim 1, wherein said antiperspirant/deodorant composition is in the form of a stick, gel, lotion, aerosol, fluid, cream, or powder.

8. A method of controlling perspiration and/or malodor of a human, the method comprising applying the antiperspirant/deodorant composition of claim 1 to the skin of a human.

* * * * *